US00RE48254E

(19) United States
(12) Reissued Patent
Slinkard et al.

(10) Patent Number: US RE48,254 E
(45) **Date of Reissued Patent: *Oct. 13, 2020**

(54) LENTIL PLANTS HAVING INCREASED RESISTANCE TO IMIDAZOLINONE HERBICIDES

(71) Applicant: University of Saskatchewan, Saskatoon (CA)

(72) Inventors: Al E Slinkard, Saskatoon (CA); Albert Vandenberg, Sasskatoon (CA); Frederick A. Holm, Saskatoon (CA)

(73) Assignee: University of Saskatchewan, Saskatoon (CA)

( * ) Notice: This patent is subject to a terminal disclaimer.

(21) Appl. No.: 14/551,314

(22) Filed: Nov. 24, 2014

Related U.S. Patent Documents

Reissue of:
(64) Patent No.: 7,232,942
Issued: Jun. 19, 2007
Appl. No.: 10/477,846
PCT Filed: May 13, 2002
PCT No.: PCT/CA02/00698
§ 371 (c)(1),
(2) Date: Nov. 14, 2003
PCT Pub. No.: WO02/092820
PCT Pub. Date: Nov. 21, 2002

U.S. Applications:
(63) Continuation of application No. 12/884,063, filed on Sep. 16, 2010, now Pat. No. Re. 45,340, which is a continuation of application No. 12/701,096, filed on Feb. 5, 2010, now abandoned, which is a continuation of application No. 12/487,402, filed on Jun. 18, 2009, now abandoned, which is an application for the reissue of Pat. No. 7,232,942.

(60) Provisional application No. 60/290,818, filed on May 14, 2001.

(51) Int. Cl.

| | |
|---|---|
| ***A01H 1/00*** | (2006.01) |
| ***A01H 5/00*** | (2018.01) |
| ***A01H 5/10*** | (2018.01) |
| ***C12N 9/88*** | (2006.01) |
| ***C12N 15/82*** | (2006.01) |

(52) U.S. Cl.
CPC ..... *C12Y 202/01006* (2013.01); *C12N 9/88* (2013.01); *C12N 15/8274* (2013.01); *C12N 15/8278* (2013.01)

(58) Field of Classification Search
CPC ..... C12N 15/8274
See application file for complete search history.

(56) References Cited

U.S. PATENT DOCUMENTS

| | | | | |
|---|---|---|---|---|
| 4,761,373 | A | 8/1988 | Anderson et al. | 800/300.1 |
| 5,013,659 | A | 5/1991 | Bedbrook et al. | 536/23.2 |
| 5,304,732 | A | 4/1994 | Anderson et al. | 800/300.1 |
| 5,331,107 | A | 7/1994 | Anderson et al. | 800/300.1 |
| 5,731,180 | A | 3/1998 | Dietrich | 800/278 |
| 5,767,361 | A | 6/1998 | Dietrich | 800/300 |
| 5,853,973 | A | 12/1998 | Kakefuda et al. | 435/4 |
| 5,928,937 | A | 7/1999 | Kakefuda et al. | 435/320.1 |
| 6,211,438 | B1 | 4/2001 | Anderson et al. | 800/300 |
| 6,211,439 | B1 | 4/2001 | Anderson et al. | 800/300 |
| 6,222,100 | B1 | 4/2001 | Anderson et al. | 800/300 |
| 6,225,105 | B1 | 5/2001 | Sathasivan et al. | 435/252.2 |
| RE45,340 | E * | 1/2015 | Slinkard | 800/260 |

FOREIGN PATENT DOCUMENTS

| | | | |
|---|---|---|---|
| EP | 0 360 750 | | 3/1990 |
| EP | 0 360 750 | A2 | 3/1990 |
| EP | 0 375 875 | | 7/1990 |
| EP | 0 375 875 | A2 * | 7/1990 |
| EP | 0 508 161 | | 10/1992 |
| EP | 0 508 161 | A1 | 10/1992 |
| EP | 0 525 384 | | 2/1993 |
| EP | 0 525 384 | A2 | 2/1993 |
| WO | WO 90/14000 | | 11/1990 |
| WO | WO 90/14000 | A1 | 11/1990 |
| WO | WO 03/013225 | | 2/2003 |
| WO | WO 03/013225 | A2 | 2/2003 |
| WO | WO 03/014356 | | 2/2003 |
| WO | WO 03/014356 | A1 | 2/2003 |
| WO | WO 03/014357 | | 2/2003 |
| WO | WO 03/014357 | A1 | 2/2003 |

OTHER PUBLICATIONS

Woodworth et al. 1996, Plant Physiology 111:S105 (Abstract 415).
Wright et al., 1998, Weed Science 46: 13-23.
Prado et al. 2004, Weed Science 52: 487-491.
Ashigh et al 2007, Weed Science 55: 558-565.
Barrett et al., (1989), "Protection of Grass Crops from Sulfonylurea and Imidazolinone Toxicity," Crop Safeners for Herbicides, *Academic Press Inc. New York*, pp. 195-220.
Li et al., (1993), "An Improved Rice Transformation System Using the Biolistic Method," *Plant Cell Rep.* 12:250-255.
Newhouse et al., (1991), "Mutations in corn (*Zea mays* L.) Conferring Resistance to Imidazolinone Herbicides," *Theor, Appl Genet.* 83:65-70.
Odell et al., (1990),"Comparison of Increased Expression of Wild-Type and Herbicide-Resistant Acetolactate Synthase Genes in Transgenic Plants, and Indication of Posttranscriptional Limitation on Enzyme Activity," *Plant Physiol.* 94:1647-1654.
Ott et al., (1996), "Rational Molecular Design and Genetic Engineering of Herbicide Resistant Crops by Structure Modeling and Site-Directed Mutagenesis of Acetohydroxyacid Synthase," *J.Mol. Biol.* 263:359-368.
Sathasivan et al., (1991), "Molecular Basis of Imidazolinone Herbicide Resistance in *Arabidopsis thaliana* var Columbia," *Plant Physiol.* 97:1044-1050.

(Continued)

*Primary Examiner* — Bruce R Campell
(74) *Attorney, Agent, or Firm* — Lowenstein Sandler LLP

(57) ABSTRACT

The present invention is directed to lentil plants having increased resistance to an imidaizolinone herbicide. One such plant described herein is the RH44 lentil variety. The present invention also includes seeds produced by these lentil plants and methods of controlling weeds in the vicinity of these lentil plants.

15 Claims, 9 Drawing Sheets

Specification includes a Sequence Listing.

(56) References Cited

OTHER PUBLICATIONS

Shaner and Robson, (1985), "Absorption, Translocation, and Metabolism of AC 252 214 in Soybean (*Glycine max*), Common Cocklebur (*Xanthium strumarium*), and Velvetleaf (*Abutilon theopbrasti*)," *Weed Sci.* 33:469-471.

Swanson et al., (1989), "Microspore Mutagenesis and Selection: Canola Plants with Field Tolerance to the Imidazolinones," *Theor. Appl. Genet.* 78:525-530.

Chang, A., and R. Duggelby, "Herbicide-resistant Forms of *Arabidopsis thaliana* Acetohydroxyacid Synthase: Characterization of the Catalytic Properties and Sensitivity to Inhibitors of Four Defined Mutants," *Biochemistry J.*, 1998, pp. 765-777, vol. 333.

Chong C., and J. Choi, "Amino Acid Residues Conferring Herbicide Tolerance in Tobacco Acetolactate Synthase," *Biomedical and Biophysical Research Communications*, 2000, pp. 462-467, vol. 279, Academic Press.

Hattori, J., et al., "Multiple Resistance to Sulfonylureas and Imidazolinones Conferred by an Acetohydroxyacid Synthase Gene with Separate Mutations for Selective Resistance," *Molecular Genetics*, 1992, pp. 167-173, vol. 232.

Mourad, G., et al., "Isolation and Genetic Analysis of a Triazolopyrimidine-Resistant Mutant of *Arabidopsis," J. Heredity*, 1993, pp. 91-96, vol. 84.

Newhouse, K., et al., "Tolerance to Imidazolinone Herbicides in Wheat," *Plant Physiology*, 1992, pp. 882-886, vol. 100.

Sathasivan, K., et al., "Nucleotide Sequence of a Mutant Acetolactate synthase Gene from an Imidaziolinone-resistant *Arabidopsis thaliana* var. Columbia," Nucleic Acids Research, 1990, pp. 2188, vol. 18(8), Oxford University Press.

Sebastian, S., et al., "Semidominant Soybean Mutation for Resistance to Sulfonylurea Herbicides," Crop. Sci., 1989, pp. 1403-1408, vol. 29.

Shaner, D., et al., "Imidazolinone-Resistant Crops: Selection, Characterization, and Management," Herbicide-Resistant Crops: Agricultural, Environmental, Economic, 1996, pp. 143-157.

Shaner, D., et al., "Imidazolinones: Potent Inhibitors of Acetohydroxyacid Synthase," *Plant Physiol.*, 1984, pp. 545-546, vol. 76.

Singh, B.K., "Biosynthesis of Valine, Leucine and Isoleucine," *Plant Amino Acids*, 1999, pp. 227-247, Marcel Dekker Inc., New York, NY.

Wright, T.R. and D. Penner, "Cell Selection and Inheritance of Imidazolinone Resistance in Sugarbeet (*Beta vulgaris*)," Theor. Appl. Genet., 1998, pp. 612-620, vol. 96, Springer-Verlag.

Duggleby, R., et al., "Systematic Characterization of Mutations in Yeast Acetohydroxyacid Synthase," *Eur. J. Biochem.*, 2003, pp. 2895-2904, vol. 270.

Lee, Y., et al., "Effect of Mutagenesis at Serine 653 of *Arabidopsis thaliana* Acetohydroxyacid Synthase on the Sensitivity to Imidazolinone and Sulfonylurea Herbicides," *FEBS Letters*, 1999, pp. 341-345, vol. 452, Federation of European Biochemical Societies.

* cited by examiner

Figure 1

The change in amino acid composition and implications for sufonylurea herbicide tolerance resulting from the gene mutation in CLEARFIELD crops conferring imidazolinone herbicide resistance

| Plant | Variety | Mutation (nucleotide change) | Locus (amino acid position) | Effect on AHAS Isozyme | Tolerant to Sulfonylurea Herbicides |
|---|---|---|---|---|---|
| Corn | XI-12 | Single gene point mutation AGC-AAC | 621 | Amino acid change serine to asparagine in AHAS isozyme | No |
| Canola | PM1 | Single gene point mutation AGC-AAC | Unknown | Amino acid change serine to asparagine in AHAS isozyme | No |
| Canola | PM2 | Single gene point mutation AGC-ATC | 557 | Amino acid change tryptophan to leucine in AHAS isozyme | Yes |
| Wheat | SWP965001 | Single gene point mutation AGC-AAC | Gene A | Amino acid change serine to asparagine in AHAS isozyme | No |

Percentage of Injury of RH44 Lentil Plants as Compared to Wild Type CDC Richlea

Figure 6

Agronomic Traits of RH44 Lentil and Various Wild Type Commercial Lentil Varieties

| Variety | Days to flowering* | Days to maturity* | Height |
|---|---|---|---|
| | | | |
| CDC Sovereign | 60 | 98 | 39.5 |
| Eston | 56 | 96(est.) | 29.8 |
| CDC Glamis | 61 | 98 | 33.5 |
| CDC Milestone | 57 | 99 | 29.5 |
| CDC Richlea | 58 | 101 | 30.8 |
| CDC Vantage | 58 | 100 | 33.5 |
| RH-44 | 58** | 101** | 33.4 |

* The data presented for flowering and maturity are a composite of data from several trials at various locations.

** The flowering and maturity data for RH44 are estimates based on observations in side-by-side trials with registered varieties.

Figure 7

Effect of 2X ODYSSEY® Application on Lentil Yield (Kernen Farm, Saskatoon, 1999 and 2000)

| | 1999 Kernen | | | 2000 Kernen | | | |
|---|---|---|---|---|---|---|---|
| Line | Yield of control | Yield with 2X ODYSSEY | % of loss from 2X ODYSSEY application | Yield of control | Yield with 2X ODYSSEY | % of loss from 2X ODYSSEY application | % of loss from 2X ODYSSEY application |
| | (g/plot) | (g/plot) | | (g/plot) | (g/plot) | | (2 years) |
| CDC Richlea | 1241 | 184 | 85 | | 185 | 82 | 83 |
| CDC Sovereign | 1064 | 229 | 81 | | 343 | 66 | 74 |
| CDC Glamis | 753 | 305 | 75 | | 411 | 59 | 67 |
| CDC Vantage | 1114 | 536 | 57 | | 370 | 63 | 60 |
| Eston | 1602 | 485 | 61 | | 532 | 47 | 54 |
| CDC Milestone | 1559 | 936 | 24 | | 500 | 50 | 37 |
| RH-44 | 1345 | 1237 | 8 | 1000 | 1011 | 0 | 4 |
| CV | | 29 | | | 31 | | |

Unsprayed mean yield of RH44 lentil in year 1999 was 1345 g/plot and 1000 g/plot in year 2000. Control plots were maintained as "weed-free" by hand-weeding plots.

Figure 8

A Comparison of the Amino Acid Composition of RH44 Lentil and Wild Type Lentil Varieties

| Test | Wild Type Lentil Varieties | | | | RH44 Lentil | | | | |
|---|---|---|---|---|---|---|---|---|---|
| | Average | Std Dev. | Min | Max | Sample 1 | Sample 2 | Sample 3 | Average | Std Dev. |
| | | % | | | | | % | | |
| Tryptophan | 0.21 | 0.02 | 0.18 | 0.24 | 0.21 | 0.20 | 0.21 | 0.21 | 0.01 |
| Cystine | 0.27 | 0.01 | 0.25 | 0.28 | 0.27 | 0.27 | 0.28 | 0.27 | 0.01 |
| Methionine | 0.20 | 0.01 | 0.19 | 0.21 | 0.20 | 0.20 | 0.20 | 0.20 | 0.00 |
| Aspartic Acid | 2.64 | 0.11 | 2.46 | 2.81 | 2.56 | 2.55 | 2.56 | 2.56 | 0.01 |
| Threonine | 0.86 | 0.03 | 0.81 | 0.92 | 0.82 | 0.83 | 0.84 | 0.83 | 0.01 |
| Serine | 1.12 | 0.03 | 1.06 | 1.17 | 1.08 | 1.08 | 1.10 | 1.09 | 0.01 |
| Glutamic Acid | 3.62 | 0.11 | 3.42 | 3.84 | 3.53 | 3.53 | 3.55 | 3.54 | 0.01 |
| Proline | 0.87 | 0.06 | 0.76 | 0.95 | 0.95 | 0.84 | 0.88 | 0.89 | 0.06 |
| Glycine | 0.93 | 0.03 | 0.88 | 0.97 | 0.93 | 0.91 | 0.93 | 0.92 | 0.01 |
| Alanine | 0.90 | 0.07 | 0.80 | 0.99 | 0.83 | 0.83 | 0.84 | 0.83 | 0.01 |
| Valine | 1.13 | 0.05 | 1.06 | 1.25 | 1.10 | 1.08 | 1.10 | 1.09 | 0.01 |
| Isoleucine | 1.00 | 0.03 | 0.95 | 1.05 | 0.96 | 0.95 | 0.97 | 0.96 | 0.01 |
| Leucine | 1.67 | 0.06 | 1.58 | 1.80 | 1.62 | 1.58 | 1.61 | 1.60 | 0.02 |
| Tyrosine | 0.45 | 0.02 | 0.40 | 0.48 | 0.44 | 0.43 | 0.45 | 0.44 | 0.01 |
| Phenylalanine | 1.12 | 0.05 | 1.04 | 1.24 | 1.08 | 1.08 | 1.08 | 1.08 | 0.00 |
| Lysine, Total | 1.56 | 0.04 | 1.49 | 1.63 | 1.51 | 1.50 | 1.53 | 1.51 | 0.02 |
| Histidine | 0.62 | 0.02 | 0.58 | 0.65 | 0.59 | 0.58 | 0.60 | 0.59 | 0.01 |
| Arginine | 1.67 | 0.09 | 1.51 | 1.84 | 1.61 | 1.57 | 1.61 | 1.60 | 0.02 |

Figure 9

A Comparison of the Nutritional Composition of RH44 Lentil and Wild Type Lentil Varieties

| Test | Wild Type Lentil Varieties | | | | RH44 Lentil | | | | |
|---|---|---|---|---|---|---|---|---|---|
| | Average | Std Dev. | Min | Max | Sample 1 | Sample 2 | Sample 3 | Average | Std Dev. |
| Moisture- Forced Draft Oven | 8.24 | 0.28 | 7.86 | 8.61 | 8.14 | 8.25 | 8.27 | 8.22 | 0.07 |
| Crude Fat/Oil | 0.76 | 0.07 | 0.63 | 0.94 | 0.82 | 0.76 | 0.76 | 0.78 | 0.03 |
| Protein | 25.22 | 0.73 | 23.97 | 26.22 | 25.04 | 23.91 | 24.50 | 24.48 | 0.57 |
| Crude Fibre | 4.31 | 0.61 | 3.10 | 5.20 | 4.90 | 4.80 | 4.70 | 4.80 | 0.10 |

LENTIL PLANTS HAVING INCREASED RESISTANCE TO IMIDAZOLINONE HERBICIDES

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATIONS

[This application is the National Stage of International Application No. PCT/C02/00698, Filed May 13, 2002; which claims the benefit of U.S. Provisional Application No. 60/290,818, filed May 14, 2001.] *This application is a continuation reissue application of continuation reissue application Ser. No. 12/884,063, filed Sep. 16, 2010, issued as U.S. Pat. No. RE45,340 on Jan. 13, 2015, which is a continuation reissue application of continuation reissue application Ser. No. 12/701,096, filed Feb. 5, 2010, now abandoned, which is a continuation reissue application of continuation reissue application Ser. No. 12/487,402, filed Jun. 18, 2009, now abandoned, which is a reissue application of U.S. Pat. No. 7,232,942, granted Jun. 19, 2007, which is the National Stage of International Application No. PCT/CA02/00698, filed May 13, 2002; which claims the benefit of U.S. Provisional Application No. 60/290,818, filed May 14, 2001, each one of which is incorporated herein by reference in its entirety.*

FIELD OF THE INVENTION

The present invention relates in general to plants having an increased resistance to imidazolinone herbicides. More specifically, the present invention relates to lentil plants obtained by mutagenesis and cross-breeding that have an increased resistance to imidazolinone herbicides.

BACKGROUND OF THE INVENTION

Imidazolinone and sulfonylurea herbicides are widely used in modem agriculture due to their effectiveness at very low application rates and relative non-toxicity in animals. Imidazolinone and sulfonylurea herbicides inhibit the activity of acetohydroxyacid synthase (AHAS), or acetolactate synthase (ALS) (E.C.4.1.3.18), the key enzyme in the biosynthesis of branch chain amino acids such as valine, leucine and isoleucine (Shaner et al. 1984 Plant Physiol. 76:545-546). By inhibiting AHAS activity, this class of herbicides prevents further growth and development of susceptible plants including many weed species. Several examples of commercially available imidazolinone herbicides are PURSUIJTS (imazethapyr), SCEPTER® (imazaquin) and ARSENAL® (imazapyr). Examples of sulfonylurea herbicides are chlorsulfiuron, metsulfuron methyl, sulfometuron methyl, chlorimuron ethyl, thifensulfuron methyl, tribenuron methyl, bensulfuron methyl, nicosulfuron, ethametsulfuron methyl, rimsulfuron, triflusulfuron methyl, triasulfuron, primisulfuron methyl, cinosulffiron, amidosulfuron, fluzasulfuron, imazosulfuron, pyrazosulfiron ethyl and halosulfuron.

Due to their high effectiveness and low-toxicity, imidazolinone herbicides are favored for application by spraying over the top of a wide area of vegetation. The ability to spray an herbicide over the top of a wide range of vegetation decreases the costs associated with plantation establishment and maintenance and decreases the need for site preparation prior to use of such chemicals. Spraying over the top of a desired tolerant species also results in the ability to achieve maximum yield potential of the desired species due to the absence of competitive species. However, the ability to use such spray-over techniques is dependent upon the presence of imidazolinone resistant species of the desired vegetation in the spray over area.

Among the major agricultural crops, some leguminous species such as soybean are naturally resistant to imidazolinone herbicides due to their ability to rapidly metabolize the herbicide compounds (Shaner and Robinson 1985 Weed Sci. 33:469-471). Other crops such as corn (Newhouse et al. 1992 Plant Physiol. 100:882-886) and rice (Barrette et al. 1989 Crop Safeners for Herbicides, Academic Press New York, pp. 195-220) are somewhat susceptible to imidazolinone herbicides. The differential sensitivity to the imidazolinone herbicides is dependent on the chemical nature of the particular herbicide and differential metabolism of the compound from a toxic to a non-toxic form in each plant (Shaner et al. 1984 Plant Physiol. 76:545-546; Brown et al. 1987 Petic. Biochm. Physiol. 27:24-29). Other plant physiological differences such as absorption and translocation also play an important role in sensitivity (Shaner and Robinson 1985 Weed Sci. 33:469-471).

Computer-based modeling of the three dimensional conformation of the AHAS-inhibitor complex predicts several amino acids in the proposed inhibitor binding pocket as sites where induced mutations would likely confer selective resistance to imidazolinones (Ott et al. 1996 J. Mol. Biol. 263:359-368). Lentil plants produced with these rationally designed mutations in the proposed binding sites of the AHAS enzyme have in fact exhibited specific resistance to a single class of herbicides (Ott et al. 1996 J. Mol. Biol. 263:359-368). Other mutations in the AHAS gene have been linked to resistance to the imidazolinone herbicides in canola (Swanson et al. 1989 Theor. Appl. Genet. 78:525-530) and com (Newhouse et al. 1991 Theor. Appl. Genet. 83:65-70).

Studies of the ALS gene in other crop plants have also resulted in sulfonylurea and imidazolinone resistance in those plants. In one report, use of a mutant ALS gene from Arabidopsis coupled with selection on sulfonylurea herbicide resulted in the production of resistant transgenic rice plants (Li et al. 1992 Plant Cell Rep. 12:250-255). An increase in in vitro resistance to chlorsulfuron of similar magnitude (200-fold) was demonstrated in transgenic rice containing a 35S/ALS transgene (Li et al. 1992 Plant Cell Rep. 12:250-255), and imidazolinone-resistant growth of transgenic tobacco was 100-fold greater than non-transformed control plants (Sathasivan et al. 1991 Plant Physiol. 97:1044-1050).

Expression of the introduced AHAS or ALS gene at different magnitudes has also been achieved by manipulating several aspects of the transformation including the use of different promoters and screening larger populations of transformants (Odell et al. 1990 Plant Physiol. 94:1647-1654; Sathasivan et al. 1991 Plant Physiol. 97:1044-1050; Li et al. 1992 Plant Cell Rep. 12:250-255). Studies showed that replacing the Arabidopsis ALS promoter with the CaMV35S promoter resulted in 40-fold differences in in vitro resistance to chlorsulfuiron (Li et al. 1992 Plant Cell Rep. 12:250-255). In tobacco, the increase in resistance to imazethapyr in individual calli transformed with a mutant ALS gene from Arabidopsis ranged from 10- to 1000-fold, most likely reflecting the differences in gene copy numbers or in chromosomal positions of the transgenes (Sathasivan et al. 1991 Plant Physiol. 97:1044-1050).

Plant resistance to imidazolinone has also been reported in a number of patents. U.S. Pat. No. 4,761,373 generally describes the use of an altered AHAS gene to elicit herbicide resistance in plants, and specifically discloses certain imidazolinone resistant corn lines. U.S. Pat. No. 5,013,659 discloses plants exhibiting herbicide resistance possessing mutations in at least one amino acid in one or more conserved regions. The mutations described therein encode either cross-resistance for imidazolinones and sulfonylureas or sulfonylurea-specific resistance, but imidazolinone-specific resistance is not described. Additionally, U.S. Pat. No. 5,731,180 and U.S. Pat. No. 5,767,361 discuss an isolated gene having a single amino acid substitution in a wild-type monocot AHAS amino acid sequence that results in imidazolinone-specific resistance.

However, to date, the prior art has not described an imidazolinone resistant pulse crop such as lentil. Pulses are the seeds of legumes that are used as food, including pea, bean, lentil, chickpea and fababean. Pulse crops, provide about 10% of the total dietary protein of the world. Lentil was one of the earliest cultivated crops in the world with archeological evidence from the early Stone Age. Lentil remains an important source of dietary protein in India, Southwest Asia and the Mediterranean, and Canadian lentil production is primarily directed toward export to these regions. While lentil is grown mainly for the seed to be harvested as a food export, the straw can also be used as a high quality animal feed or as a source of organic material for soil improvement. Cultivated varieties of lentil (Lens culinaris) are believed to descend from Lens orientalis, the only wild-type species able to naturally cross with Lens culinaris and produce fully fertile progeny.

A major challenge in lentil production is weed control. Lentil seedlings are short and slow-growing in relation to many weed species and therefore compete very poorly. Effective chemical weed control is necessary for commercial viability. The ability to spray over an herbicide that kills a broad spectrum of broadleaf weeds, either as a pre-emergent spray or as a post-emergent spray, would be beneficial to lentil production. Even more advantageous would be an herbicide that also controls a broad spectrum of grassy weeds and volunteer cereals that could be applied over a broad area of lentil crops.

Therefore, what are needed in the art are lentil plants having increased resistance to herbicides such as imidazolinone and methods for controlling weed growth in the vicinity of lentil plants. Such compositions and methods would allow for the use of spray over techniques when applying herbicides to areas containing lentil plants.

SUMMARY OF THE INVENTION

The present invention relates to lentil plants having increased resistance to an imidazolinone herbicide as compared to a wild type variety of the plant. The lentil plant described herein can be any member of the Lens genus, including, but not limited to, Lens culinaris Medikus, Lens orientalis (Boiss.) Hand.-Maz., Lens nigricans (M; Bieb.) Grand., Lens ervoides (Bring.) Grand., Lens odemensis Ladiz., Lens lamotiei Czefranova, Lens tomentosus Ladiz and hybrids thereof. Additionally, the imidazolinone herbicide referred to herein can be selected from, but is not limited to, imazethapyr, imazapic, imazamox, imazaquin, imazethabenz and imazapyr.

In one embodiment of the present invention, the lentil plant variety is designated RH44 and has a Patent Deposit Designation Number PTA-3270. The present invention also includes a mutant, recombinant, or genetically engineered derivative of the plant with Patent Deposit Designation Number PTA-3270, any progeny of the plant with Patent Deposit Designation Number PTA-3270 and a plant that is the progeny of any of these plants. In further preferred embodiments, the lentil plant also has the herbicide resistance characteristics of the plant with Patent Deposit Designation Number PTA-3270.

Included in the present invention are hybrids of the RH44 line described herein and another lentil variety including, but not limited to, CDC Richlea, CDC Robin, CDC Sovereign, CDC Glamis, CDC Milestone, CDC Vantage, Eston, Laird, Spanish Brown and French Green.

In addition to lentil plants having increased resistance to imidazolinone herbicides, the present invention also encompasses plant parts, plant cells and plant seeds derived from these plants. In one embodiment, the lentil plant seed is true breeding for an increased resistance to an imidazolinone herbicide as compared to a wild type variety of the lentil plant seed.

The methods of the present invention include methods for controlling weeds within the vicinity of a lentil plant, comprising applying an imidazolinone herbicide to the weeds and to the lentil plant, wherein the lentil plant has increased resistance to the imidazolinone herbicide as compared to a wild type variety of the lentil plant.

BRIEF DESCRIPTION OF THE DRAWINGS

FIG. 1 is a table showing the effects of amino acid substitutions in the AHAS isoenzyme on the herbicide resistance of various plants.

FIG. 6 is a table showing the agronomic characteristics of RH44 lentil plants and various wild type commercial lentil varieties.

FIG. 7 is a table showing the increased resistance of RH44 lentil plants to ODYSSEY herbicide as compared to various wild type commercial lentil varieties.

FIG. 8 is a table showing the amino acid composition of RH44 lentil plants and various wild type commercial lentil varieties.

FIG. 9 is a table showing the nutritional composition of RH44 lentil plants as compared to other registered commercial lentil varieties.

DETAILED DESCRIPTION

Figure 2:
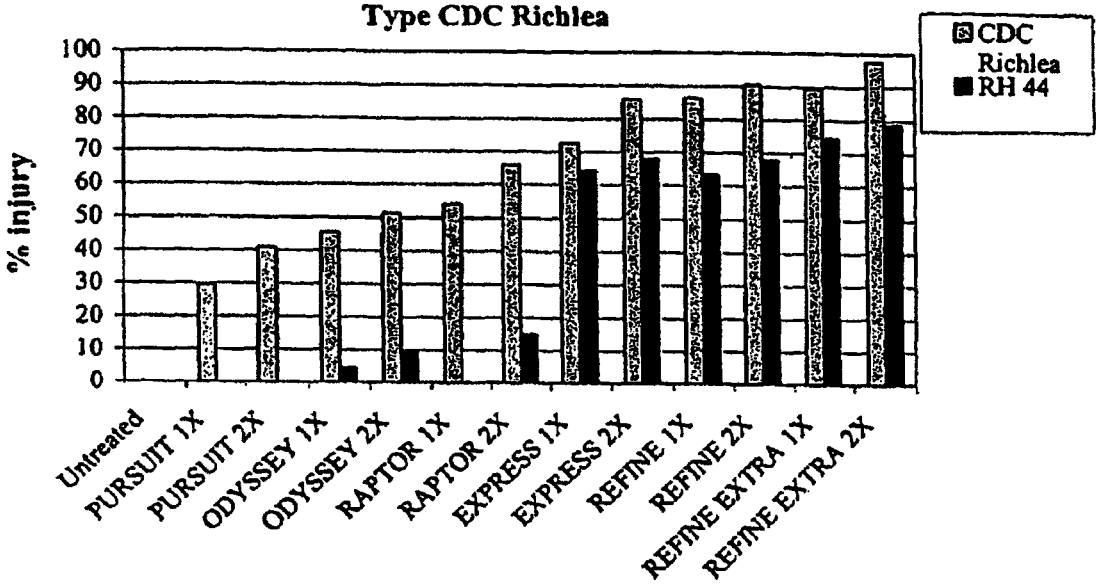
FIG. 2 is a graph showing the percentage injury to RH44 lentil plants and the wild type CDC Richlea lentil variety when sprayed in the seedling stage with various rates of imidazolinone or sulfonylurea herbicides.

The present invention is directed to lentil plants, lentil plant parts and lentil plant cells having increased resistance to imidazolinone herbicides. In one embodiment, a wild type lentil plant is one which is a member of the Lens genus and does carry the dominant gene for resistance to an imidazolinone herbicide. The present invention also includes seeds produced by the lentil plants described herein and methods for controlling weeds in the vicinity of the lentil plants described herein. It is to be understood that as used in the specification and in the claims, "a" or "an" can mean one or more, depending upon the context in which it is used. Thus, for example, reference to "a cell" can mean that at least one cell can be utilized.

As used herein, the term "lentil plant" refers to a plant that is a member of the Lens genus of the Leguinosae family. The lentil plants of the present invention can be members of the Lens genus including, but not limited to, Lens culinaris Medikus, Lens orientalis (Boiss.) Hand.-Maz., Lens nigricans (M. Bieb.) Grand., Lens ervoides (Bring.) Grand., Lens odemensis Ladiz., Lens lamoittie Czefranova and Lens tomentosus Ladiz. (Ladizinsky et al. 1984, van Oss et al., 1997) and hybrids thereof. The term "lentil plant" is intended to encompass lentil plants at any stage of maturity or development as well as any tissues or organs taken or derived from any such plant unless otherwise clearly indicated by context. Plant tissues and organs include, but are not limited to, leaves, seeds, stems, flowers, roots, single cells, gametes, anther cultures, calli cultures, tissue cultures and protoplasts. In particular, the present invention includes seeds produced by the lentil plants of the present invention. In one embodiment, the seeds are true breeding for an increased resistance to an imidazolinone herbicide as compared to a wild type Variety of the lentil plant seed.

The present invention describes a lentil plant having increased resistance to an imidazolinone herbicide as compared to a wild type variety of the plant. The Examples below provide a detailed description of the mutagenesis, breeding and selection of lentil plants having such increased resistance to an imidazolinone herbicide. One plant derived from these procedures is deposited with the ATCC (Patent Deposit Designation Number PTA-3270) and designated herein as the RH44 lentil variety. A deposit of 2500 seeds of the RH44 lentil variety was made with the American Type Culture Collection, Manassas, Va. on Mar. 20, 2001. This deposit was made in accordance with the terms and provisions of the Budapest Treaty relating to the deposit of microorganisms. The deposit was made for a term of at least thirty years and at least five years after the most recent request for the furnishing of a sample of the deposit is received by the ATCC. The deposited seeds were accorded Patent Deposit Designation Number PTA-3270.

The present invention includes the lentil plant having a Patent Deposit Designation Number PTA-3270; a mutant, recombinant, or genetically engineered derivative of the plant with Patent Deposit Designation Number PTA-3270; any progeny of the plant with Patent Deposit Designation Number PTA-3270; and a plant that is the progeny of any of these plants. In a preferred embodiment, the lentil plant of the present invention additionally has the herbicide resistance characteristics of the plant with Patent Deposit Designation Number PTA-3270.

*The acetohydroxyacid synthase large subunit (AHASL) gene of the RH44 lentil line was sequenced and found to contain a single mutation that gives rise to the A205V (using the Arabidopsis thaliana AHASL1 amino acid position nomenclature amino acid substitution in the AHASL protein, when compared to wild-type AHASL protein. Thus, a plant of the RH44 lentil line comprises a mutant AHASL gene that encodes an AHASL protein comprising a valine at the position that corresponds to amino acid 205 in the Arabidopsis thaliana AHASL1. In a wild-type AHASL protein, amino acid 205 is known to be alanine.*

Also included in the present invention are hybrids of the RH44 line described herein and another lentil variety including, but not limited to, CDC Richlea, CDC Robin, CDC Sovereign, CDC Glamis, CDC Milestone, CDC Vantage, Eston, Laird, Spanish Brown and French Green. The term "variety" refers to a group of plants within a species that share constant characters that separate them from the typical form and from other possible varieties within that species. While possessing at least one distinctive trait, a variety is also characterized by some variation between individuals within the variety, based primarily on the Mendelian segregation of traits among the progeny of succeeding generations. A variety is considered "true breeding" for a particular trait if it is genetically homozygous for that trait to the extent that, when the true-breeding variety is self-pollinated, a significant amount of independent segregation of the trait among the progeny is not observed. In the present invention, the trait arises from a dominant mutation in an AHAS gene of the lentil plant or seed.

In one embodiment of the present invention, the lentil plant having increased resistance to an imidazolinone herbicide comprises an altered AHAS nucleic acid. As used herein, the term "altered AHAS nucleic acid" refers to an AHAS nucleic acid that is mutated from an AHAS nucleic acid in a wild type lentil plant and that confers increased imidazolinone resistance to a plant in which it is transcribed. In a preferred embodiment, the altered AHAS nucleic acid comprises a serine to asparagine amino acid substitution. In a more preferred embodiment, the altered AHAS nucleic acid comprises a serine to asparagine amino acid substitution in an AHAS gene. In a still further preferred embodiment, the serine to asparagine amino acid substitution corresponds to the serine to asparagine amino acid substitutions found in other AHAS gene paralogs that display imidazolinone resistance. Examples of such mutated AHAS gene paralogs include those found in wheat variety SWP965001, corn variety XI-12 and canola variety PM1, all of which have increased resistance to imidazolinone herbicides and are described in FIG. 1. By "AHAS nucleic acid" is meant a RNA or DNA sequence that encodes or directs the expression of an AHAS protein, and may include a coding region and its corresponding untranslated 5' and 3' sequence regions; Additionally, "AHAS gene" refers specifically to a DNA sequence that encodes or directs the expression of an AHAS protein.

It is to be understood that the lentil plant of the present invention can comprise a wild type or unaltered AHAS gene in addition to an altered AHAS gene. As described in Example 3, it is contemplated that the mutation in lentil variety RH44 contains a mutation in only one of two AHAS isoenzymes. Therefore, the present invention includes a lentil plant comprising one or more altered AHAS nucleic acids.

As also used herein, the term "AHAS protein" refers to an acetohydroxyacid synthase protein and the term "altered AHAS protein" refers to any AHAS protein that is mutated from a wild type AHAS protein and that confers increased imidazolinone resistance to a plant, plant cell, plant part, plant seed or plant tissue when it is expressed therein. The imidazolinone herbicide can be selected from, but is not limited to, PURSUIT® (imazethapyr), CADRE® (imazapic), RAPTOR® (imazamox), SCEPTER® (imazaquin), ASSERT® (imazethabenz), ARSENAL® (imazapyr) ODYSSEY® (imazapyr/imazamox), or a derivative thereof.

In addition to the compositions of the present invention, the present invention provides a method of controlling weeds growing in the vicinity of the lentil plants described above. These methods comprise applying imidazolinone herbicides to weeds in the vicinity of lentil plants having an increased resistance to an imidazolinone herbicide as compared to a wild type variety of the plant. In a preferred embodiment, the lentil plant comprises a altered AHAS nucleic acid. In a more preferred embodiment, the altered AHAS nucleic acid comprises a serine to asparagine amino acid substitution in an AHAS gene. In a still further preferred embodiment, the serine to asparagine amino acid substitution corresponds to the serine to asparagine amino acid substitutions found in other AHAS gene paralogs that display imidazolinone resistance.

As described above, the present invention teaches compositions and methods for increasing the imidazolinone resistance of a lentil plant or seed as compared to a wild-type variety of the plant or seed. In a preferred embodiment, the imidazolinone resistance of a lentil plant or seed is increased such that the plant or seed can withstand an imidazolinone herbicide application of preferably approximately 1-28 ounces, more preferably approximately 3-14 ounces, and most preferably approximately 6, 7, or 8 ounces of active ingredient per acre.

By providing for lentil plants having increased resistance to imidazolinone, a wide variety of formulations can be employed for protecting lentil plants from weeds, so as to enhance plant growth and reduce competition for nutrients. An imidazolinone herbicide can be used by itself for post-emergence control of weeds in areas surrounding the lentil plants described herein or an imidazolinone herbicide formulation can be used that contains other additives. Such additives include other herbicides, detergents, adjuvants, spreading agents, sticking agents, stabilizing agents, or the like. The imidazolinone herbicide formulation can be a wet or dry preparation and can include, but is not limited to, flowable powders, emulsifiable concentrates and liquid concentrates. The imidazolinone herbicide and herbicide formulations can be applied in accordance with conventional methods, for example, by spraying, irrigation, dusting, or the like.

It should be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims. Additionally, all references cited herein are hereby expressly incorporated herein by reference.

EXAMPLES

Example 1

Mutagenesis of Mixed Lentil Seed and Selection of RH44 Lentil Variety Having Increased Resistance to Imidazolinone Herbicides, Lentil line RH44 was derived from a bulk of mixed $F_3$ lentil (Lens culinaris) seed developed via conventional crossing followed by self-pollination. Five kilograms of bulk, mixed seed were treated in EMS solution and then planted in the field as the $M_1$ generation. $M_2$ seeds were harvested from the field-grown $M_1$ plants. $M_2$ plants were advanced to the $M_3$ generation. $M_3$ seed was planted on 1 hectare (ha). Prior to flowering, the field was sprayed with 2×ODYSSEY® herbicide. At harvest, approximately 300 surviving plants were harvested and threshed. Approximately 150 plants were selected for further evaluation by planting a sample of seed from each plant in pots in growth rooms. These plants were sprayed with 2×ODYSSEY® herbicide at four weeks after emergence. Eight pots were selected for field evaluation. Seed of each line was sown in a small field plot and then sprayed with 2×ODYSSEY®. Line RH44 was selected as having imidazolinone resistance derived from a population of approximately one million $M_3$ seeds. Since the original mutagen dose was small, the $M_3$ population size was large, and the modification rate was relatively low (1:150,000), it is unlikely that multiple modifications occurred in RH44 to contribute to any deleterious effects (Konzak, 1987 Induced mutations in wheat improvement. In: Heyne, E. G. (ed.) Wheat and Wheat Improvement. American Society of Agronomy, Madison, Wis. pp. 428-443). FIG. 2 shows the increased imidazolinone resistance of the RH44 line as compared to the CDC Richlea lentil variety. FIG. 2 also shows that the RH44 line has little resistance to sulfonylureas such as EXPRESS, REFINE and REFINE EXTRA. The results in FIG. 2 reflect tolerance readings taken two weeks after application of the herbicide. The designations "1×" and "2×" refer to commercial application rates of those products.

Example 2

Analysis of Mutation in Lentil Variety RH44

The available data strongly indicates that a mutation in a single gene similar to that observed in wheat, corn and canola is responsible for the observed imidazolinone tolerance in the RH44 variety of lentil. In wheat, the AHAS isozymes have been labeled as genes A, B and C. The mutation responsible for imidazolinone tolerance in wheat is due to a point mutation of AGC to AAC at a single site in AHAS gene A (FIG. 1). This site corresponds to the maize amino acid position 621 previously identified in X1-12 (imidazolinone-tolerant maize). This single nucleotide change of a guanine to an adenine results in a single amino acid change serine to asparagine (FIG. 1). Additionally, the imidazolinone tolerance trait in CLEARFIELD® canola is controlled by two semi-dominant genes PM1 and PM2. Resistance to the PM1 mutant is conferred through a guanine to adenine point mutation in the AHAS1 gene. This results in a similar single amino acid change from serine to asparagine. A different point mutation is responsible for the resistance observed in the PM2 mutant. A guanine to threonine change in AHAS3 results in a tryptophan to leucine amino acid change.

The serine to asparagine amino acid substitution results in a plant that is tolerant to imidazolinone herbicides, but not sulfonylureas (Newhouse et al. 1992 Plant Physiol. 100: 882 -886). This is true of wheat, corn and canola. Similarly, the RH44 lentil variety is similarly not tolerant to sulfonylurea herbicides, suggesting that a similar guanine to adenine point mutation produced a serine to asparagine amino acid substitution similar to the other CLEARFIELD® D varieties X1-12, corn, PM1 canola and SWP965001 wheat (FIG. 1).

Example 3

Herbicide Resistance of the RH44 Lentil Variety

Figure 3:
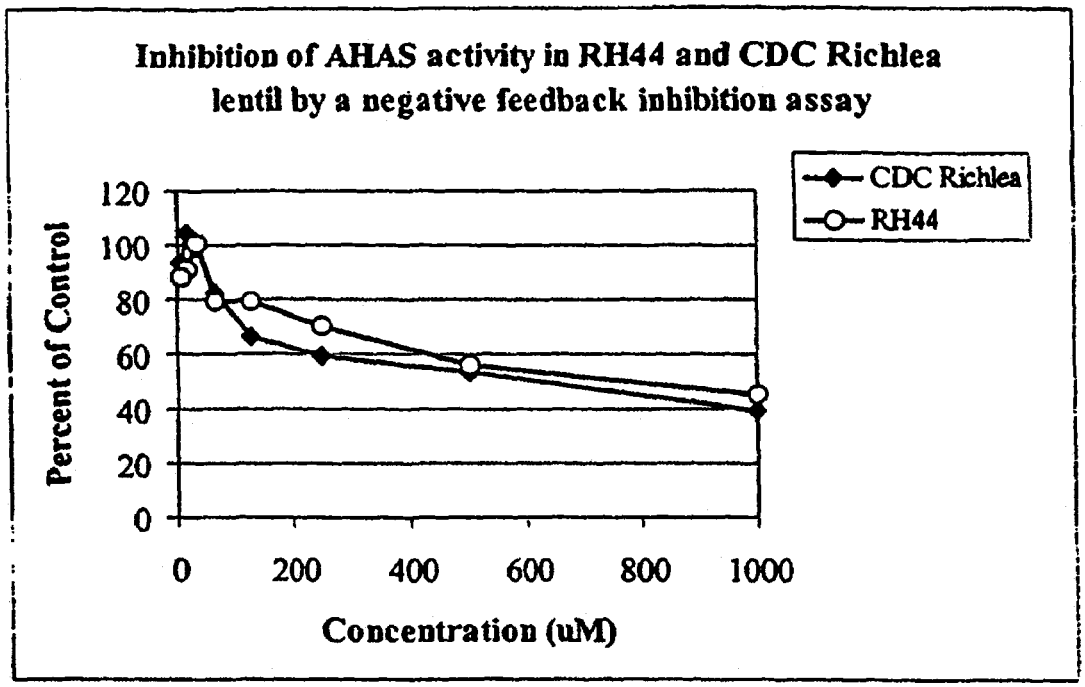
FIG. 3 is a graph showing the inhibition of AHAS activity in RH44 and CDC Richlea lentil plants by a negative feedback inhibition assay.

The responses of the RH44 lentil variety and the CDC Richlea variety were identical in a negative feedback inhibition assay. As described earlier, AHAS is an enzyme active in the biosynthesis of leucine and valine. Under conditions of excess leucine and/or valine, the activity of AHAS is diminished. The ability of leucine and valine addition to inhibit AHAS activity was the same in the RH44 lentil and CDC Richlea lentil varieties, indicating very similar levels of expression and a lack of any discernible difference in AHAS function (FIG. 3).

Figure 4:
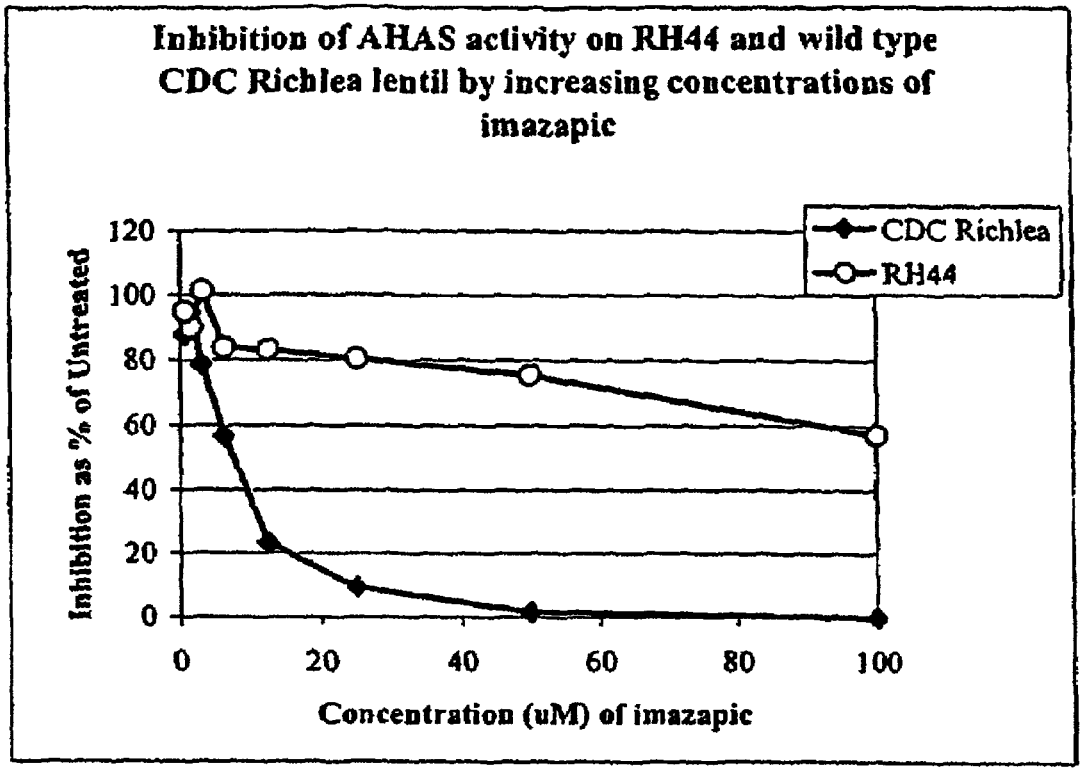
FIG. 4 is a graph showing the inhibition of AHAS activity in RH44 and CDC Richlea lentil plants by increasing concentrations of imazapic.
Figure 5:
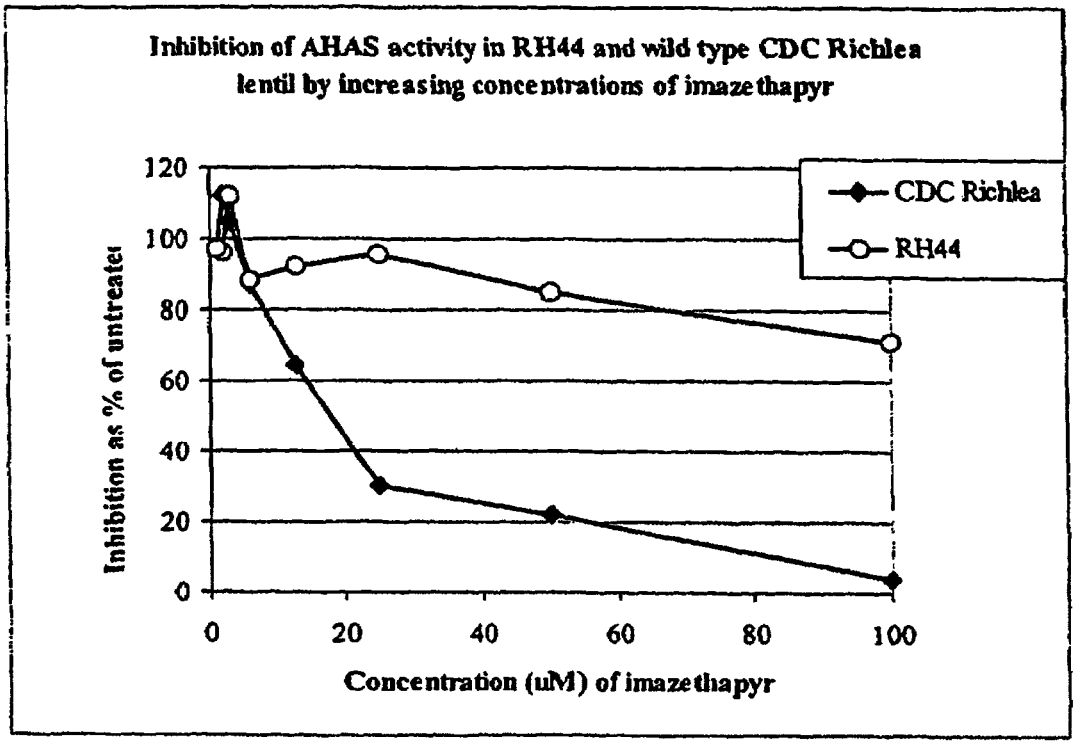
FIG. 5 is a graph showing the inhibition of AHAS activity in RH44 and CDC Richlea lentil plants by increasing concentrations of imazethapyr.

The AHAS activity in the wild type CDC Richlea lentil variety was inhibited by imazapic (CADRE®)) (FIG. 4) and imazethapyr (PURSUIT®) (FIG. 5) representative of all imidazolinone herbicides. The AHAS activity in the RH44 lentil variety was also inhibited by the addition of the two imidazolinone herbicides, but not to the same extent as for the wild type lentil CDC Richlea.

These results suggest the existence of a semi-dominant AHAS isozyme in the RH44 lentil variety that is encoded by genes similar to those in X1-12 corn, SWP965001 wheat and PM1 canola. It is therefore likely that the gene primarily responsible for AHAS activity in the RH44 lentil has undergone a point mutation similar to that observed in corn, wheat and canola. This has made the isozyme coded for by this sequence resistant to imidazolinone inhibition. The wild type isozyme has no such mutation and therefore is susceptible to imidazolinone herbicide. Such a scenario would explain why AHAS activity drops 30 to 40% with the addition of maximum concentrations of imidazolinone herbicides. The resistance trait was determined to be stable in the mutagenized line RH44 lentil variety indicating that the resistance trait is semi-dominant, also similar to the imidazolinone resistant trait in canola.

Example 4

Agronomic Characteristics of the RH44 Lentil Variety

The agronomic traits (yield, height, time to maturity) of the RH44 lentil variety were similar to most of the commercial wild type cultivars of lentil. The time to flowering was approximately 58 days, the time to maturity was approximately 100 days and the mean height was 30 to 35 cm (FIG. 6). Both the RH44 lentil variety and CDC Richlea lentil variety are relatively high yielding, however, they are both susceptible to ascochyta blight and anthracnose.

Initial field evaluation of RH44 lentil indicates that the seed yield is similar to that of CDC Richlea and superior to some commercial varieties (FIG. 7). In field trials, the RH44 lentil has commercially viable phenotypic and agronomic properties. Harvested RH44 lentil seeds were mixed in appearance. Some seeds had a 'mottled' seed coat while some remained clear. Selection of seeds on the basis of appearance resulted in a mixed harvest in subsequent generations, which is a phenotypic trait similar to the Eston lentil variety.

Example 5

Amino Acid Composition of Imidazolinone-Tolerant Lentil

An analysis of the amino acid composition was conducted to compare the RH44 lentil variety with existing registered wild type lentil varieties in order to determine if any significant differences existed (FIG. 8). The seed for analysis was obtained from trials conducted in the year 2000 where RH44 lentil and several other lentil varieties were grown under the same conditions. Amino acid composition was determined using AOAC Method 982.30 D,E,F by Woodson-Tenent Laboratories, Inc. The results of this analysis demonstrated the similarity in amino acid composition among all varieties of lentil, many of which have very different phenotypic characteristics. This analysis also demonstrated that the mutation leading to imidazolinone tolerance in lentil produces no change outside the range of natural variability in the amino acid composition of lentils.

*The lentil plant of the present invention, the seeds of which have been deposited under the Patent Deposit Designation Number PTA-3270, comprise the amino acid sequence (SEQ ID NO: 1) of the mature herbicide-tolerant AHAS protein in RH44 lentil plant from amino acid residue 87 to amino acid 661. These amino acids correspond to amino acid residues 96-670 of Arabidopsis thaliana AHAS.*

Example 6

Nutritional Analysis of Imidazolinone-Tolerant Lentil

A proximate analysis was conducted to compare the RH44 lentil variety with existing registered wild type lentil varieties in order to determine if any significant differences in nutritional value existed (FIG. 9). The seed for analysis was obtained from trials conducted in the year 2000 where RH44 lentil and several other lentil varieties were grown under the same conditions. The results of this analysis demonstrate the similarity in many nutritional characteristics among varieties of lentil, several of which have very different phenotypic characteristics. This analysis also demonstrates that the mutation leading to imidazolinone tolerance in RH44 lentil produces no subsequent change in the moisture, fat, fiber or protein content of lentil seed. The RH44 lentil is changed in its AHAS activity, but is unchanged in nutritional/food safety attributes when compared to commercial wild type lentil varieties in Canada.

SEQUENCE LISTING

```
<160> NUMBER OF SEQ ID NOS: 1

<210> SEQ ID NO 1
<211> LENGTH: 575
<212> TYPE: PRT
<213> ORGANISM: Lens culinaris

<400> SEQUENCE: 1

Pro Arg Lys Gly Ala Asp Ile Leu Val Glu Ala Leu Glu Arg Gln Gly
1               5                   10                  15

Val Thr Asn Val Phe Ala Tyr Pro Gly Gly Ala Ser Met Glu Ile His
            20                  25                  30
```

```
Gln Ala Leu Thr Arg Ser Lys Thr Ile Arg Asn Ile Leu Pro Arg His
        35                  40                  45

Glu Gln Gly Gly Val Phe Ala Ala Glu Gly Tyr Ala Arg Ser Ser Gly
    50                  55                  60

Leu Pro Gly Val Cys Ile Ala Thr Ser Gly Pro Gly Ala Thr Asn Leu
65                  70                  75                  80

Val Ser Gly Leu Ala Asp Ala Leu Met Asp Ser Val Pro Leu Val Ala
                85                  90                  95

Ile Thr Gly Gln Val Pro Arg Arg Met Ile Gly Thr Asp Val Phe Gln
            100                 105                 110

Glu Thr Pro Ile Val Glu Val Thr Arg Ser Ile Thr Lys His Asn Tyr
        115                 120                 125

Leu Ile Leu Asp Val Asp Asp Ile Pro Arg Val Val Lys Glu Ala Phe
    130                 135                 140

Phe Leu Ala Thr Ser Gly Arg Pro Gly Pro Val Leu Ile Asp Val Pro
145                 150                 155                 160

Lys Asp Ile Gln Gln Gln Leu Ala Val Pro Asn Trp Ala Glu Pro Ile
                165                 170                 175

Lys Leu Thr Gly Tyr Val Ser Arg Leu Pro Lys Ile Pro Asp Glu Ser
            180                 185                 190

Gln Phe Glu Gln Val Val Arg Leu Leu Leu Glu Ser Lys Lys Pro Val
        195                 200                 205

Leu Tyr Val Gly Gly Gly Cys Leu Asn Ser Ser Glu Glu Leu Asn Arg
    210                 215                 220

Phe Val Glu Leu Thr Gly Ile Pro Val Ala Ser Thr Leu Met Gly Leu
225                 230                 235                 240

Gly Ser Tyr Pro Ile Gly Gly Glu His Ser Leu His Met Leu Gly Met
                245                 250                 255

His Gly Thr Val Tyr Ala Asn Tyr Ala Val Asp Ser Ser Asp Leu Leu
            260                 265                 270

Leu Ala Phe Gly Val Arg Phe Asp Asp Arg Val Thr Gly Lys Leu Glu
        275                 280                 285

Ala Phe Ala Ser Arg Ala Lys Ile Val His Ile Asp Ile Asp Ser Ala
    290                 295                 300

Glu Ile Gly Lys Asn Lys Ile Pro His Met Ser Ile Cys Ala Asp Met
305                 310                 315                 320

Lys Val Ala Leu Glu Gly Leu Asn Arg Val Leu Glu Ser Lys Gly Val
                325                 330                 335

Lys Gly Lys Leu Asp Phe Glu Ala Trp Arg Gln Glu Leu Asn Val Gln
            340                 345                 350

Lys Leu Lys Phe Pro Leu Gly Phe Lys Thr Phe Glu Asn Ala Ile Ser
        355                 360                 365

Pro Gln Tyr Ala Ile Gln Val Leu Asp Glu Leu Thr Asn Gly Asp Ala
    370                 375                 380

Ile Ile Ser Thr Gly Val Gly Gln His Gln Met Trp Ala Ala Gln Phe
385                 390                 395                 400

Tyr Glu Tyr Lys Arg Pro Arg Gln Trp Leu Thr Ser Gly Gly Leu Gly
                405                 410                 415

Ala Met Gly Phe Gly Leu Pro Ala Ala Ile Gly Ala Ala Val Ala Asn
            420                 425                 430

Pro Asn Ala Val Val Val Asp Ile Asp Gly Asp Gly Ser Phe Ile Met
        435                 440                 445
```

-continued

```
Asn Val Gln Glu Leu Ala Thr Ile Arg Val Glu Asn Leu Pro Ile Lys
    450                 455                 460

Ile Leu Leu Leu Asn Asn Gln His Leu Gly Met Val Val Gln Trp Glu
465                 470                 475                 480

Asp Arg Phe Tyr Lys Ser Asn Arg Gly His Thr Tyr Leu Gly Asp Pro
                485                 490                 495

Ser Arg Glu Glu Glu Ile Phe Pro Asn Met Leu Gly Phe Ala Asp Ala
            500                 505                 510

Cys Gly Ile Pro Ala Ala Arg Val Thr Lys Lys Glu Glu Leu Arg Glu
        515                 520                 525

Ala Ile Gln Lys Met Leu Asp Thr Pro Gly Pro Tyr Leu Leu Asp Val
    530                 535                 540

Ile Thr Pro His Gln Glu His Val Leu Pro Met Ile Pro Ser Asn Gly
545                 550                 555                 560

Ser Phe Lys Asp Val Ile Thr Glu Gly Asp Gly Arg Thr Ser Tyr
                565                 570                 575
```

What is claimed is:

[1. A lentil plant having increased resistance to an imidazolinone herbicide as compared to a wild type variety of the plant, wherein the lentil plant has an ATCC Patent Deposit Designation Number PTA-3270.]

[2. A method for controlling weeds within the vicinity of the lentil plant of claim 1, comprising applying an imidazolinone herbicide to the weeds and to the lentil plant.]

[3. The method of claim 2, wherein the imidazolinone herbicide is selected from the group consisting of imazethapyr, imazapic, imazamox, imazaquin, imazethabenz and imazapyr.]

[4. The method of claim 2, wherein the imidazolinone herbicide is imazethapyr.]

[5. The method of claim 2, wherein the imidazolinone herbicide is imazamox.]

[6. A seed of lentil line RH44, representative seed of said line having been deposited under ATCC Patent Deposit Designation Number PTA-3270.]

[7. A lentil plant, or a part thereof, produced by growing the seed of claim 6.]

[8. A method for producing a hybrid lentil seed wherein the method comprises crossing the plant of claim 7 with a different lentil plant and harvesting the resulting hybrid lentil seed.]

[9. A hybrid lentil seed produced by the method of claim 8.]

[10. A lentil plant, or a part thereof, produced by growing the seed of claim 9.]

[11. A method for controlling weeds within the vicinity of a lentil plant, the method comprising applying an imidazolinone herbicide to the weeds and to the lentil plant, wherein the lentil plant is produced by growing a seed of lentil line RH44, representative seed of said line having been deposited under ATCC Patent Deposit Designation Number PTA-3270.]

[12. The method of claim 11 , wherein the imidazolinone herbicide is selected from the group consisting of imazethapyr, imazapic, imazamox, imazaquin, imazethabenz and imazapyr.]

[13. The method of claim 11, wherein the imidazolinone herbicide is imazethapyr.]

[14. The method of claim 11, wherein the imidazolinone herbicide is imazamox.]

*15. A method for controlling weeds within the vicinity of a lentil plant, comprising applying a composition comprising an imidazolinone herbicide to the weeds and the lentil plant, wherein the lentil plant has been obtained by a process comprising crossing lentil line RH44, a representative seed of said line having been deposited under ATCC Patent Deposit Designation Number PTA-3270, with another Lens culinaris variety, wherein the plant comprises an AHAS polypeptide comprising the amino acid sequence as set forth in SEQ ID NO:1.*

*16. The method of claim 15, wherein said imidazolinone herbicide comprises at least one of: imazethapyr, imazapic, imazamox, imazaquin, imazethabenz or imazapyr.*

*17. The method of claim 15, wherein the imidazolinone herbicide comprises imazethapyr.*

*18. The method of claim 15, wherein the imidazolinone herbicide comprises imazamox.*

*19. The method of claim 15, wherein said plant is transgenic.*

*20. A lentil seed of a lentil plant, said lentil plant having increased resistance to an imidazolinone herbicide as compared to that of a wild type variety of the plant, wherein the lentil plant has been obtained by a process comprising crossing lentil line RH44, a representative seed of said line having been deposited under ATCC Patent Deposit Designation Number PTA-3270, with another Lens culinaris variety, wherein the plant comprises an AHAS polypeptide comprising the amino acid sequence as set forth in SEQ ID NO: 1.*

*21. The lentil seed of claim 20, wherein said lentil seed is transgenic.*

*22. The lentil seed of claim 20, wherein said lentil plant is a hybrid.*

*23. The lentil seed of claim 20, wherein the process further comprises a step of self pollination.*

*24. The lentil seed of claim 20, wherein the lentil plant is true breeding for the herbicide resistance characteristics of lentil line RH44.*

*25. A method for selecting a lentil plant comprising applying a composition comprising an imidazolinone herbicide to the lentil plant wherein the lentil plant has been obtained by a process comprising crossing lentil line RH44, a representative seed of said line having been deposited under ATCC Patent Deposit Designation Number PTA-*

*3270, with another Lens culinaris variety, wherein the plant comprises an AHAS polypeptide comprising the amino acid sequence as set forth in SEQ ID NO: 1.*

*26. The method of claim 25, wherein said imidazolinone herbicide comprises at least one of: imazethapyr, imazapic, imazamox, imazaquin, imazethabenz or imazapyr.*

*27. The method of claim 25, wherein the imidazolinone herbicide comprises imazethapyr.*

*28. The method of claim 25, wherein the imidazolinone herbicide comprises imazamox.*

*29. The method of claim 25, wherein said plant is transgenic.*

* * * * *